(12) United States Patent
Naclerio

(10) Patent No.: US 12,064,195 B2
(45) Date of Patent: Aug. 20, 2024

(54) POWER MANAGEMENT SCHEMES FOR SURGICAL SYSTEMS

(71) Applicant: Covidien LP, Mansfield, MA (US)

(72) Inventor: Edward C. Naclerio, Madison, CT (US)

(73) Assignee: Covidien LP, Mansfield, MA (US)

( * ) Notice: Subject to any disclaimer, the term of this patent is extended or adjusted under 35 U.S.C. 154(b) by 496 days.

(21) Appl. No.: 17/602,026

(22) PCT Filed: Apr. 2, 2020

(86) PCT No.: PCT/US2020/026363
§ 371 (c)(1),
(2) Date: Oct. 7, 2021

(87) PCT Pub. No.: WO2020/210106
PCT Pub. Date: Oct. 15, 2020

(65) Prior Publication Data
US 2022/0142723 A1 May 12, 2022

Related U.S. Application Data

(60) Provisional application No. 62/830,596, filed on Apr. 8, 2019.

(51) Int. Cl.
*A61B 34/30* (2016.01)
*A61B 34/37* (2016.01)
(Continued)

(52) U.S. Cl.
CPC ............ *A61B 34/30* (2016.02); *B25J 9/1689* (2013.01); *H02J 9/061* (2013.01); *A61B 34/37* (2016.02)

(58) Field of Classification Search
CPC .................... A61B 34/30; A61B 34/37; A61B 2018/00178; A61B 2560/0204;
(Continued)

(56) References Cited

U.S. PATENT DOCUMENTS 9,685,820 B2 6/2017 Kolhatkar et al.
2007/0114852 A1 5/2007 Lin et al.
(Continued)

FOREIGN PATENT DOCUMENTS

CN 206063215 U 4/2017
CN 108464863 A 8/2018
(Continued)

OTHER PUBLICATIONS

Extended European Search Report issued in corresponding application EP 20787435.5 dated Dec. 15, 2022 (7 pages).
(Continued)

*Primary Examiner* — Ryan Johnson
(74) *Attorney, Agent, or Firm* — Carter, DeLuca & Farrell LLP

(57) ABSTRACT

A surgical robotic system includes a robotic arm having at least one surgical instrument and a control device coupled to the robotic arm and configured to control the robotic arm, the control device including one or more components. The surgical robotic system also includes a power supply having: a tower power supply chassis configured to supply first direct current to the robotic arm; a power distribution unit configured to supply second direct current to the one or more components; a first uninterruptable power supply device coupled to the tower power supply chassis and configured to receive a first alternating current from a first alternating current input; and a second uninterruptable power supply device coupled to the power distribution unit and configured to receive a second alternating current from a second alternating current input.

17 Claims, 2 Drawing Sheets

(51) Int. Cl.
*B25J 9/16* (2006.01)
*H02J 9/06* (2006.01)

(58) Field of Classification Search
CPC . A61B 2560/0214; B25J 9/1689; B25J 19/00; H02J 2310/23; H02J 9/061; H02J 9/06
See application file for complete search history.

(56) References Cited

U.S. PATENT DOCUMENTS

| | | |
|---|---|---|
| 2008/0302200 A1 | 12/2008 | Tobey |
| 2010/0228249 A1 | 9/2010 | Mohr et al. |
| 2011/0305049 A1 | 12/2011 | Raptis et al. |
| 2013/0217967 A1 | 8/2013 | Mohr et al. |
| 2016/0294210 A1 | 10/2016 | Nguyen |
| 2017/0348062 A1 | 12/2017 | Sweeney, II et al. |
| 2018/0228553 A1* | 8/2018 | Bai .................. A61B 34/30 |
| 2020/0138534 A1* | 5/2020 | Garcia Kilroy ........ A61B 34/70 |

FOREIGN PATENT DOCUMENTS

| | | |
|---|---|---|
| CN | 109330687 A | 2/2019 |
| WO | 2014191724 A1 | 12/2014 |
| WO | 2015088569 A1 | 6/2015 |

OTHER PUBLICATIONS

International Search Report and Written Opinion dated Jul. 10, 2020 issued in corresponding PCT Appln. No. PCT/US2020/026363.
Office Action issued in corresponding Chinese Application No. 202080015749.7 dated Apr. 15, 2023, together with English language translation (13 pages).

* cited by examiner

POWER MANAGEMENT SCHEMES FOR SURGICAL SYSTEMS

CROSS-REFERENCE TO RELATED APPLICATION

This application is a National Stage Application under 35 U.S.C. § 371(a) of PCT/US2020/026363, filed Apr. 2, 2020, which claims the benefit of and priority to U.S. Provisional Application No. 62/830,596, filed Apr. 8, 2019. The entire contents of all of the foregoing applications are incorporated by reference herein.

BACKGROUND

Surgical robotic systems are currently being used in minimally invasive medical procedures. Some surgical robotic systems may include a console supporting a surgical robotic arm and a surgical instrument having an end effector (e.g., forceps or grasping tool) coupled to the robotic arm, which is actuated by the robotic arm. Such robotic systems are powered by complex electrical power supply systems with multiple electrical supply rails and backup units. Thus, there is a need for a streamlined power management scheme for surgical robotic systems to control complex electrical power supplies.

SUMMARY

The present disclosure provides a power management system for surgical robotic systems. Certain power supplies for powering robots include multiple powered components controlled by a single shut-off switch (e.g., 3-pole switch) to turn power on and off to all of the multiple loads simultaneously. However, this configuration is inflexible in certain respects and prevents selective activation and deactivation of certain loads in response to situations where some of the loads needed to be turned off while the remaining loads need to be turned on. The present disclosure provides for a power management architecture that allows for independent activation and deactivation of powered components energizing the loads.

In addition, single shut-off switch architectures that include uninterruptible power supplies ("UPS"), which includes one or more electrical batteries, also tend to suffer due to the batteries becoming drained if unpowered for prolonged periods of time. Even though the shut-off switch isolates the loads from the UPSs, since the UPSs remain in a running condition their batteries are depleted after AC mains are disconnected. The present power management architecture provides for communication between individual components of the power supply and their respective UPSs to turn off each UPS based on demands of the load.

According to one embodiment of the present disclosure, a surgical robotic system is disclosed, which includes a robotic arm having at least one surgical instrument and a control device coupled to the robotic arm and configured to control the robotic arm, the control device including one or more components. The surgical robotic system also includes a power supply having: a tower power supply chassis configured to supply first direct current to the robotic arm; a power distribution unit configured to supply second direct current to the one or more components; a first uninterruptable power supply device coupled to the tower power supply chassis and configured to receive a first alternating current from a first alternating current input; and a second uninterruptable power supply device coupled to the power distribution unit and configured to receive a second alternating current from a second alternating current input.

According to one aspect of the above embodiment, the surgical robotic system also includes a power ingress module interconnecting the first alternating current input and the second alternating current input with the first uninterruptible power supply device and the second uninterruptible power supply device, respectively. The power ingress module is configured to disconnect the first alternating current input and the second alternating current input from the first uninterruptible power supply device and the second uninterruptible power supply device, respectively.

According to another aspect of the above embodiment, the component is one of a core controller, a safety controller, a visualization controller, a visualization system, a display, a network adapter, a light source, or a camera control unit.

According to another aspect of the above embodiment, the component is a core controller and each of the core controller and the tower power supply chassis is configured to detect connection or disconnection of the power supply to at least one of the first alternating current input or the second alternating current input. The surgical robotic system also includes one of a stationary support base or a movable support base, wherein the robotic arm is coupled to one of the stationary support base or the movable support base. The core controller and the tower power supply chassis are configured to detect connection or disconnection of the power supply to at least one of the stationary support base or the movable support base.

According to one aspect of the above embodiment, the surgical robotic system also includes an electrosurgical generator and a foot switch emulator interconnecting the electrosurgical generator and the power ingress module. The foot switch emulator is configured to receive a third alternating current from a third alternating current input.

According to another embodiment of the present disclosure, a power supply for a surgical robotic system is disclosed. The power supply includes: a tower power supply chassis configured to supply first direct current to a robotic arm; a power distribution unit configured to supply second direct current to a control device configured to control the robotic arm; a first uninterruptable power supply device coupled to the tower power supply chassis and configured to receive a first alternating current from a first alternating current input; and a second uninterruptable power supply device coupled to the power distribution unit and configured to receive a second alternating current from a second alternating current input.

According to one aspect of the above embodiment, the power supply further includes a power ingress module interconnecting the first alternating current input and the second alternating current input with the first uninterruptible power supply device and the second uninterruptible power supply device, respectively. The power ingress module is configured to disconnect the first alternating current input and the second alternating current input from the first uninterruptible power supply device and the second uninterruptible power supply device, respectively. The power distribution unit is coupled to at least one component selected from a core controller, a safety controller, a visualization controller, a visualization system, a display, a network adapter, a light source, or a camera control unit. In embodiments, the at least one component is a core controller and each of the core controller and the tower power supply chassis is configured to detect connection or disconnection of the power supply to at least one of the first alternating current input or the second alternating current input. In embodiments, each of the core controller and the tower power supply chassis is configured to detect connection or disconnection of the power supply to a support base.

According to another aspect of the above embodiment, the power supply further includes a foot switch emulator interconnecting an electrosurgical generator and the power ingress module. The foot switch emulator is configured to receive a third alternating current from a third alternating current input.

BRIEF DESCRIPTION OF THE DRAWINGS

Embodiments of the present disclosure are described herein with reference to the accompanying drawings, wherein.

DETAILED DESCRIPTION

Figure 1:
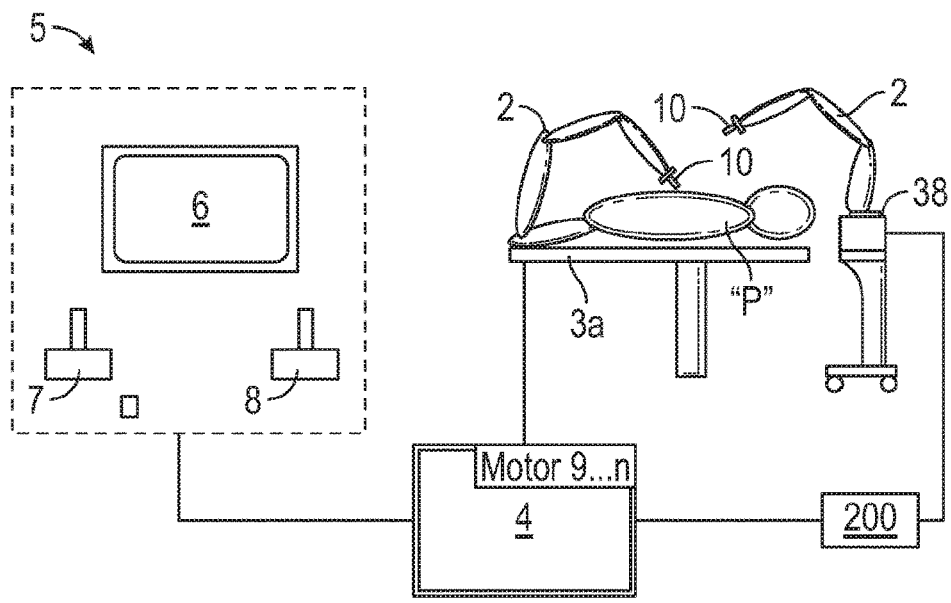
FIG. 1 is a schematic illustration of a surgical robotic system including a surgical robotic arm according to the present disclosure.

Embodiments of the presently disclosed surgical robotic systems are described in detail with reference to the drawings, in which like reference numerals designate identical or corresponding elements in each of the several views. As used herein the term "distal" refers to the portion of the surgical robotic system and/or the surgical instrument coupled thereto that is closer to the patient, while the term "proximal" refers to the portion that is farther from the patient.

Although the following description is specific to a surgical robotic system, the power supply described below may be used in any suitable medical device requiring electrical power. Referring initially to FIG. 1, a surgical robotic system 1 includes a plurality of robotic arms 2, each having a surgical instrument 10 removably attached thereto; a control device 4; and an operating console 5 coupled to control device 4. Surgical robotic system 1 is configured for use on a patient "P" lying on a stationary support base, such as a surgical table 3a to be treated in a minimally invasive manner using the surgical instrument 10. The robotic arm 2 may be attached either to a stationary support base, such as the table 3a or a movable support base, such as a movable cart 3b. The surgical robotic system 1 also includes a power supply 200 configured to provide electrical power to the robotic arm 2 and the control device 4. In embodiments, depending on the proximity of the operating console 5 (e.g., whether the operating console 5 is disposed in the operating room or remotely) the power supply 200 may be also coupled to the operating console 5.

Operating console 5 includes a display device 6, which displays the surgical site and manual input devices 7, 8, by which a clinician is able to remotely control robotic arms 2. Each of the robotic arms 2 may be composed of a plurality of links, which are connected through joints. Robotic arms 2 may be driven by electric drives (not shown) that are connected to control device 4. Control device 4 (e.g., a computer, a logic controller, etc.) is configured to activate the drives, based on a set of programmable instructions stored in memory, in such a way that robotic arms 2 and surgical instruments 10 execute a desired movement according to a movement in response to input from manual input devices 7, 8.

The control device 4 may include one or more processors (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processors may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processors may be substituted for by using any logic circuit adapted to execute algorithms, calculations, and/or set of instructions described herein.

Control device 4 may control a plurality of motors 9 . . . n, each of which is configured to actuate the surgical instrument 10 to effect operation and/or movement of surgical instrument 10. It is contemplated that control device 4 coordinates the activation of the motors 9 . . . n to coordinate a clockwise or counter-clockwise rotation of drive members (not shown) to coordinate operation and/or movement of the surgical instrument 10. In embodiments, each motor of the plurality of motors 9 . . . n can be configured to actuate a drive rod, cable, or a lever arm (not shown) to effect operation and/or movement of each surgical instrument 10. In embodiments, motors 9 . . . n may include embedded control electronics integrated within the motor housings obviate the reliance on the control device 4.

For a detailed discussion of the construction and operation of a surgical robotic system, reference may be made to U.S. Pat. No. 8,828,023, the entire contents of which are incorporated by reference herein.

Figure 2:
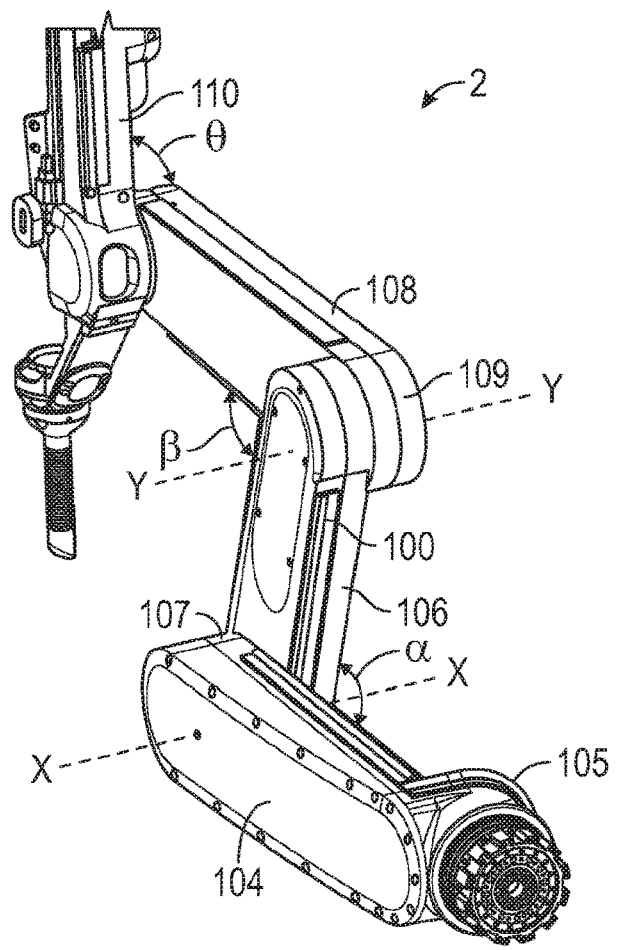
FIG. 2 is a perspective view of a surgical robotic arm of the surgical robotic system of FIG. 1 according to the present disclosure.

With reference to FIG. 2, the robotic arm 2 includes a plurality of movable links, a first link 104, a second link 106, a third link 108, and a holder 110, which are coupled to each other by actuators (not shown) allowing for movement of the robotic arm 2 into various configurations. The holder 110 is configured to receive an instrument drive unit which is configured to couple to an actuation mechanism of the surgical instrument 10. Instrument drive unit transfers actuation forces from its motors to the surgical instrument 10 to actuate components (e.g., end effectors) of the surgical instrument 10.

The first link 104 includes a curved base 105 configured to secure the robotic arm 2 to the table 3a or the movable cart 3b (FIG. 1). The second link 106 is rotatable at a joint 107 and about an axis "X-X" relative to the first link 104, such that an angle α defined by the first and second links 104 and 106 is from about 0° to about 140°. The third link 108 is rotatable at a joint 109 and about an axis "Y-Y" relative to the second link 106, such that an angle β defined by the second and third links 106 and 108 is from about 0° to about 140°. The holder 110 is rotatable relative to the third link 108 such that an angle θ defined by the holder 110 and the third link 108 is from about 25° to about 160°.

Figure 3:
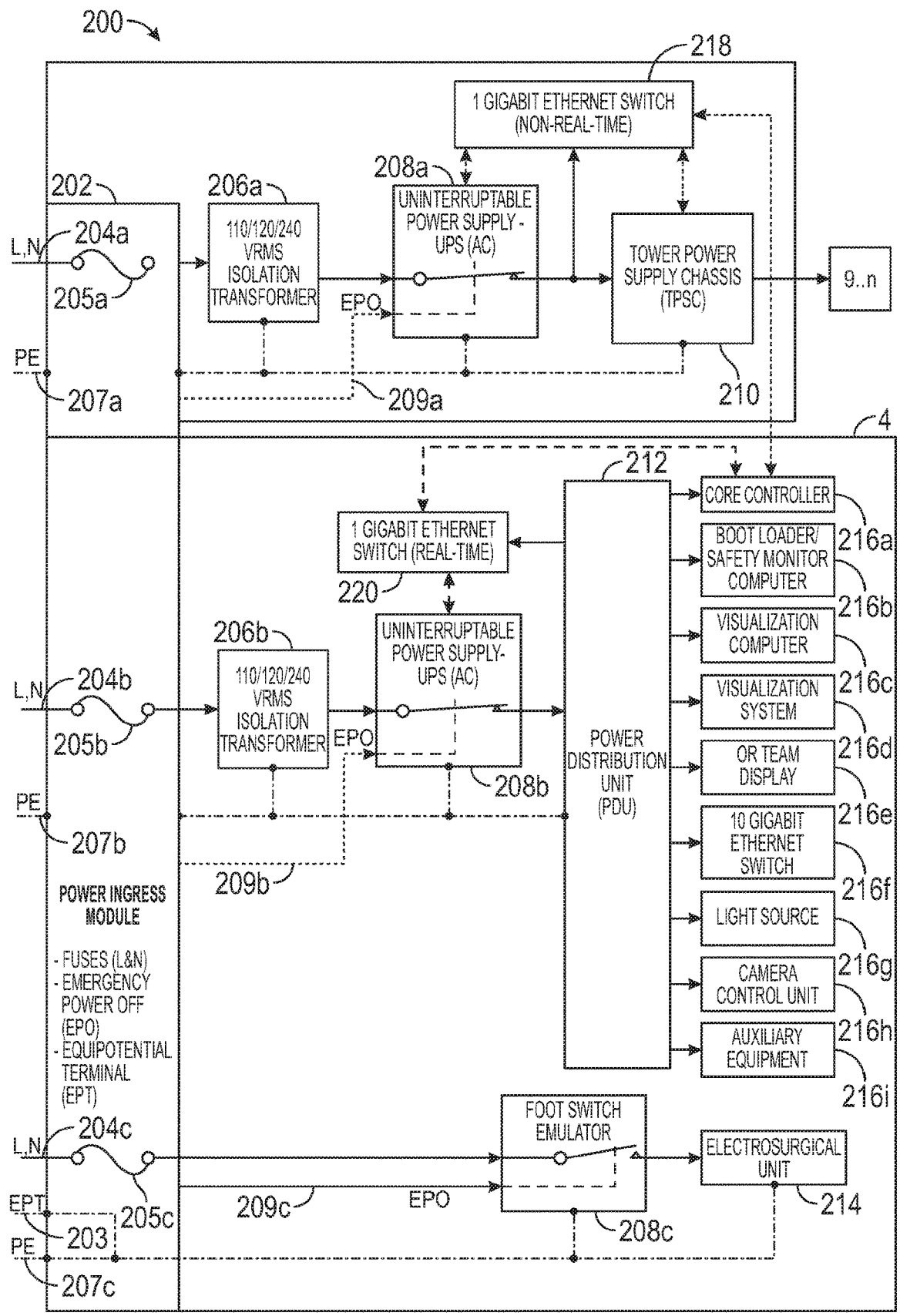
FIG. 3 is a schematic electrical circuit diagram of a power supply according to the present disclosure.

The robotic arm 2 is coupled to the power supply 200 (FIG. 1), which provides electrical regulated power to the robotic arm 2 as well as the motors 9 . . . n. With reference to FIG. 3, a power supply 200 includes a power ingress module 202, which is coupled to one or more AC line inputs 204a, 204b, 204c. Each of the AC line inputs 204a-c includes line and neutral connections which are coupled to each other through a fuse 205a, 205b, 205c, respectively, to provide for overcurrent protection. In addition, each of the AC line inputs 204a-c also includes a protective earth connection 207a, 207b, 207c, respectively. The power ingress module 202 also includes an equipotential terminal 203 to provide for common ground.

Each of the AC line inputs 204a and 204b is also coupled to a corresponding isolation transformer 206a and 206b of the power supply and the control device 4, respectively, for electrical safety purposes and to uninterruptible power supplies ("UPS") 208a and 208b, which provide backup electrical power. In particular, the UPSs 208a and 208b are coupled to a tower power supply chassis ("TPSC") 210 and power distribution unit ("PDU") 212, respectively. In some embodiments, the TPSC 210 may be also configured to couple to the table 3a or the movable cart 3b. Thus, the TPSC 210 powers motors and other electromechanical actuators of the robotic arm 2.

The AC line input 204a supplies electrical power to the TPSC 210, the AC line input 204b supplies electrical power to the PDU 212, and the AC line input 204c supplies electrical power to an electrosurgical generator 214 through a foot switch emulator 208c, which is used to provide an activation signal to the electrosurgical generator 214. Each of the UPS 208a and 208b as well as the foot switch emulator 208c is coupled to a corresponding emergency power off connections 209a, 209b, 209c, respectively, allowing for disconnection of the UPSs 208a and 208b.

The PDU 212 powers various control, input, and communication components of the control device 4, such as a core controller 216a, a safety controller 216b, a visualization controller 216c, a visualization system 216d, a display 216e, a network adapter 216f, a light source 216g, a camera control unit 216h, and other auxiliary equipment 216i.

The power supply 200 also includes a first network switch 218 coupled to the UPS 208a and a second network switch 220 coupled to the UPS 208b. The first and second network switches 218 and 220 may be any suitable local area networking device, either wired, such as ethernet, or wireless, such as WiFi. The core controller 216a is coupled to the first and second network switches 218 and 220. In addition, the first network switch 218 is coupled to the TPSC 210. Thus, the first network switch 218 provides for bidirectional communication with the UPS 208a, the TPSC 210, and the core controller 216a and the second network switch 220 provides for bidirectional communication with the UPS 208b and the core controller 216a. In addition, the first and second network switches 218a and 218b also interconnect the control device 4, the operating console 5, the robotic arm 2, and the power supply 200.

The core controller 216a is configured to operate in a low power mode and monitor the UPSs 208a and 208b to determine if the power supply 200 is still connected to AC line inputs 204a, 204b, 204c. Thus, when the surgical robotic system 1 is shut down, e.g., upon completion of a surgical procedure, allowing the core controller 216a to continue operation. In the event the AC line inputs 204a, 204b, 204c are disconnected, the core controller 216a is also configured to control the UPSs 208a and 208b to turn off completely to preserve the battery charge. In addition, the first and second network switches 218 and 220 are also configured to be powered on following disconnection from the AC line inputs 204a, 204b, 204c. This allows for a faster startup time since the first and second network switches 218 and 220 no longer would have to boot up.

In situations where AC line inputs 204a, 204b, 204c are disconnected from the power supply 200 during a surgical procedure, the UPSs 208a and 208b are configured to maintain AC power to the components connected to the power supply 200 until the core controller 216a initiates a shutdown of all system components including the UPSs 208a and 208b under operator control, or if the UPSs 208a and 208b are about to be depleted.

If AC line inputs 204a, 204b, 204c are disconnected from the power supply 200, the core controller 216a is configured to monitor the UPSs 208a and 208b and detect the disconnection of AC line inputs 204a, 204b, 204c. The core controller 216a is also configured to command the UPSs 208a and 208b to shut down following a short delay to allow for recovery from accidental disconnection.

The TPSC 210 is operational when it is connected to the AC line input 204a through the UPS 208a. The TPSC 210 is configured to connect to the table 3a and/or the movable cart 3b to provide power thereto and to the robotic arm 2. The TPSC 210 is configured detect whether or not it is connected to the table 3a and/or movable cart 3b, such that electrical power is supplied to the table 3a and/or movable cart 3b after the TPSC 210 is attached thereto. Thus, if AC line input 204a is disconnected from the TPSC 210 and the TPSC 210 is not connected to either table 3a and/or movable cart 3b, the TPSC 210 commands the UPS 208a to turn off and preserve the battery charge.

When the movable cart 3b is connected to the TPSC 210, the TPSC 210 is configured to detect which port the movable cart 3b is connected to and to enable the respective output from the AC/DC converter (not shown) to supply power to the movable cart 3b. Similarly, when the movable cart 3b is disconnected from the TPSC 210, the TPSC 210 is configured to detect which port the movable cart 3b was disconnected from and disable the respective output from the AC/DC converter that powered the movable cart 3b.

The TPSC 210 is also configured to monitor the UPS 208a and detect the loss of the AC line inputs 204a, 204b, 204c. The TPSC 210 is configured to command the UPS 208a to shut down following a short delay period to allow for recovery from accidental disconnection.

The power supply 200 according to the present disclosure provides for a faster startup time and better preservation of the charged state of the batteries in the UPSs 208a and 208b. The first network switch 218 allows the TPSC 210 to communicate with the UPS 208a regardless of the powered state of the rest of the power supply 200, e.g., the PDU 212, since the UPSs 208a and 208b are controlled by their corresponding components that receive power therefrom. In addition, the UPSs 208a and 208b as well as the TPSC 210 are configured to monitor power consumption. This data is collected and is used during operation of the surgical robotic system 1 and during fault detection and handling. The core controller 216a is also configured to access this data through the first and second network switches 218a and 218b.

The power supply 200 is configured to operate in multiple operational states as described in further detail below. Initially, the AC line inputs 204a, 204b, 204c are connected to the power supply 200, without the surgical robotic system 1 being set up or used for a surgical procedure. Since the AC line inputs 204a and 204b are connected the UPSs 208a and 208b are charging their respective batteries. The TPSC 210 and the core controller 216a are also operational at this time and monitor their respective UPSs 208a and 208b to determine whether the AC line inputs 204a and 204b are connected. The core controller 216a also monitors whether a system activation signal is received, e.g., from a system activation button, to initiate system startup. In embodiments, the system activation button (not shown) may be disposed on the control device 4 and/or the operating console 5.

The first and second network switches 218a and 218b are also powered and operational. The safety controller 216b, the visualization controller 216c, the visualization system 216d, the display 216e, the network adapter 216f, the light source 216g, the camera control unit 216h, and other auxiliary equipment 216i may be turned off by the user to conserve power. The foot switch emulator 208c is also powered up, but the electrosurgical generator 214 is turned off.

As noted above, the control device 4 may be used to activate the surgical robotic system 1. The activation process commences with the core controller 216a starting up the control device 4 and its computing components to prepare for the surgical procedure as well as any of the following systems that may have been previously powered down, the safety controller 216b, the visualization controller 216c, the visualization system 216d, the display 216e, the network adapter 216f, the light source 216g, the camera control unit 216h, and other auxiliary equipment 216i. In addition, the core controller 216a also notifies the operating console 5 that the startup process was initiated.

Since the first and second network switches 218a and 218b were previously powered on, the ready time for the control device 4 is shortened and depends on the boot up of the remaining systems, e.g., boot up time, operating system and application time load times, etc. At this point, the core controller 216a also attempts to communicate with the movable cart 3b as described above.

The operating console 5 may also be used to activate the surgical robotic system 1. Once the user presses the system activation button on the operating console 5, a signal is sent by the operating console 5 to the core controller 216a since the first and second network switches 218a and 218b are powered on and connect the operating consoler 5 to the core controller 216a. The core controller 216a then starts up the control device 4 and its computing components to prepare for the surgical procedure as well as any of the following systems that may have been previously powered down, the safety controller 216b, the visualization controller 216c, the visualization system 216d, the display 216e, the network adapter 216f, the light source 216g, the camera control unit 216h, and other auxiliary equipment 216i. The core controller 216a also attempts to establish communication with the movable cart 3b and send a message to the operating console 5 that the surgical robotic system 1.

After the surgical robotic system 1 is activated through the control device 4 and/or the operating console 5, the surgical robotic system 1 is used to perform a surgical procedure. Upon completion of the surgical procedure, the operating console 5 prompts the user to power off the electrosurgical generator 214, the light source 216g, and the camera control unit 216h. The safety controller 216b and the visualization controller 216c may also enter a low power condition or power off completely. The core controller 216a also commands the operating console 5 to shut down.

During operation, the user may press an emergency power off button (not shown), which may be disposed on the control device 4 and/or the operation console 5 to activate emergency power off connections 209a, 209b, 209c, which disconnect the AC line inputs 204a, 204b, 204c from the TPSC 210, the PDU 212, and the electrosurgical generator 214. More specifically, the UPSs 208a and 208b interrupt supply of AC from AC line inputs 204a, 204b, 204c being supplied to TPSC 210 and the PDU 212. To recover from emergency power shut down, each of the UPSs 208a and 208b may then be powered on manually by the user.

It will be understood that various modifications may be made to the embodiments disclosed herein. In embodiments, the sensors may be disposed on any suitable portion of the robotic arm. Therefore, the above description should not be construed as limiting, but merely as exemplifications of various embodiments. Those skilled in the art will envision other modifications within the scope and spirit of the claims appended thereto.

The invention claimed is:

1. A surgical robotic system comprising:
   a robotic arm including at least one surgical instrument;
   a control device coupled to the robotic arm and configured to control the robotic arm, the control device including at least one component;
   a power supply including:
      a tower power supply chassis configured to supply first direct current to the robotic arm;
      a power distribution unit configured to supply second direct current to the at least one component;
      a first uninterruptable power supply device coupled to the tower power supply chassis and configured to receive a first alternating current from a first alternating current input; and
      a second uninterruptable power supply device coupled to the power distribution unit and configured to receive a second alternating current from a second alternating current input.

2. The surgical robotic system according to claim 1, further comprising:
   a power ingress module interconnecting the first alternating current input and the second alternating current input with the first uninterruptible power supply device and the second uninterruptible power supply device, respectively.

3. The surgical robotic system according to claim 2, wherein the power ingress module is configured to disconnect the first alternating current input and the second alternating current input from the first uninterruptible power supply device and the second uninterruptible power supply device, respectively.

4. The surgical robotic system according to claim 1, wherein the at least one component is selected from the group consisting of a core controller, a safety controller, a visualization controller, a visualization system, a display, a network adapter, a light source, and a camera control unit.

5. The surgical robotic system according to claim 1, wherein the at least one component is a core controller and each of the core controller and the tower power supply chassis are configured to detect connection or disconnection of the power supply to at least one of the first alternating current input or the second alternating current input.

6. The surgical robotic system according to claim 5, further comprising at least one of a stationary support base or a movable support base, wherein the robotic arm is coupled to at least one of the stationary support base or the movable support base.

7. The surgical robotic system according to claim 6, wherein each of the core controller and the tower power supply chassis are configured to detect connection or disconnection of the power supply to at least one of the stationary support base or the movable support base.

8. The surgical robotic system according to claim 2, further comprising an electrosurgical generator and a foot switch emulator interconnecting the electrosurgical generator and the power ingress module.

9. The surgical robotic system according to claim 8, wherein the foot switch emulator is configured to receive a third alternating current from a third alternating current input.

10. A power supply for a surgical robotic system, the power supply comprising:
   a tower power supply chassis configured to supply first direct current to a robotic arm;
   a power distribution unit configured to supply second direct current to a control device configured to control the robotic arm;
   a first uninterruptable power supply device coupled to the tower power supply chassis and configured to receive a first alternating current from a first alternating current input; and
   a second uninterruptable power supply device coupled to the power distribution unit and configured to receive a second alternating current from a second alternating current input.

11. The power supply according to claim 10, further comprising:
   a power ingress module interconnecting the first alternating current input and the second alternating current input with the first uninterruptible power supply device and the second uninterruptible power supply device, respectively.

12. The power supply according to claim 11, wherein the power ingress module is configured to disconnect the first alternating current input and the second alternating current input from the first uninterruptible power supply device and the second uninterruptible power supply device, respectively.

13. The power supply according to claim 10, wherein power distribution unit is coupled to at least one component selected from the group consisting of a core controller, a safety controller, a visualization controller, a visualization system, a display, a network adapter, a light source, and a camera control unit.

14. The power supply according to claim 13, wherein the at least one component is a core controller and each of the core controller and the tower power supply chassis are configured to detect connection or disconnection of the power supply to at least one of the first alternating current input or the second alternating current input.

15. The power supply according to claim 13, wherein each of the core controller and the tower power supply chassis are configured to detect connection or disconnection of the power supply to a support base.

16. The power supply according to claim 11, further comprising a foot switch emulator interconnecting an electrosurgical generator and the power ingress module.

17. The power supply according to claim 16, wherein the foot switch emulator is configured to receive a third alternating current from a third alternating current input.

* * * * *